United States Patent

Manwaring et al.

[11] Patent Number: 5,566,681
[45] Date of Patent: Oct. 22, 1996

[54] APPARATUS AND METHOD FOR STABILIZING A BODY PART

[76] Inventors: Kim H. Manwaring, 3440 E. Tonto Dr., Ahwatukee, Ariz. 85044; Mark L. Manwaring, SW. 1430 Wadleigh Dr., Pullman, Wash. 99163

[21] Appl. No.: 433,238

[22] Filed: May 2, 1995

[51] Int. Cl.⁶ ..................................... A61G 15/00
[52] U.S. Cl. .......................... 128/845; 606/130
[58] Field of Search ..................... 128/845, 846, 128/857, 858, 869, 870; 606/130

[56] References Cited

U.S. PATENT DOCUMENTS 5,383,454   1/1995   Bucholz .............................. 128/653.1

OTHER PUBLICATIONS

WFR Aquaplast Corporation, "Opti–Mold™ Re–Usable U–Frame Headholders", 1994, brochure.

Primary Examiner—Michael A. Brown
Attorney, Agent, or Firm—Meschkow & Gresham, P.L.C.

[57] ABSTRACT

An apparatus for non-invasively stabilizing the head of a patient is provided. The apparatus includes a support frame, a rigid template mounted to the support frame, a plurality of fiducial marker housings located on the support frame, and a mounting assembly that attaches the support frame to a table or a bed. The rigid template is formed by molding a heat-activated sheet of plastic around the head or face of the patient. A method for treating the head of a patient is also provided. The method involves forming a rigid template that conforms to the head and/or face of a patient, positioning the head with the rigid template, performing a radiographic imaging procedure, and performing a subsequent surgical procedure. The imaging and surgical procedures are performed with the patient stabilized in the same position.

10 Claims, 4 Drawing Sheets

APPARATUS AND METHOD FOR STABILIZING A BODY PART

FIELD OF THE INVENTION

The present invention relates in general to medical devices. In particular, the present invention relates to medical devices for stabilizing a body part in connection with medical procedures.

BACKGROUND OF THE INVENTION

Many medical procedures, including surgery and radiographic imaging, require the stabilization or immobilization of specific body parts. Other medical techniques, such as frameless stereotaxy or delivery of ionizing radiation, require the precise placement of reference (fiducial) markers on or proximate to a body part. Traditional stabilization or positioning techniques for procedures on body parts other than the head include providing padded supports or contoured mattresses. However, when the cranium is involved, the traditional techniques are not completely effective.

One commonly accepted procedure immobilizes the head with a number of invasive fixating pins. Although cranial fixation with invasive pins is adequate for some medical procedures, its use may be undesirable for other applications. For example, typical equipment for implementing pin fixation may be bulky or cumbersome, which can cause access problems during surgery or other medical procedures. As another example, the use of fixating pins involves piercing the skin and embedding the pins into the cranium, which may cause medical complications. In addition, if the patient is an infant or a young child, then the skull is soft and deformable. In such cases, the fixating pins can easily puncture or distort the skull, or may inadequately stabilize the skull for medical procedures. Furthermore, many medical procedures require the patient to be repeatedly immobilized in the same position. With such procedures, repeated pin fixation may be undesirable because of the inherent risk of complications and the inexactness of repositioning the head. Thus, there is a need for an alternative technique for the positioning of the head.

A common medical procedure involves taking radiographic images (such as CT, PET, or MRI scans) of a body part for examination before performing surgery and for use during surgery. Frameless stereotaxy procedures provide localization information to surgeons while they are operating, without the cumbersome equipment associated with frame-based stereotaxy procedures. In addition, modern computer image guided surgery techniques provide surgeons with real-time feedback and images obtained from radiographic imaging procedures during surgery. Fiducial markers are typically utilized during stereotactic and imaging processes to provide reference points for guidance during surgery. Prior art methods typically involve the application of fiducial markers directly to the body part or to a positioning apparatus.

Frameless stereotactic techniques typically require the relative positions of the body part and fiducial markers to be identical during the radiographic imaging and subsequent surgical procedures. However, prior art locating or immobilization techniques often fail to achieve this result. In addition, as mentioned above, although pin fixation may provide adequate immobilization during both imaging and surgery, it is not preferred when the patient is an infant or a child. Therefore, there is a need for an improved locating technique that can accurately position a body part during radiographic imaging and subsequent surgery.

SUMMARY OF THE INVENTION

Accordingly, it is an advantage of the present invention that an improved apparatus and method for positioning a body part are provided.

A further advantage of the present invention is that an improved apparatus and method for stabilizing a body part are provided that can be utilized to stabilize the head of an infant or a child.

Another advantage of the present invention is that a method and apparatus are provided that can be utilized to repeatedly position reference markers relative to a body part.

Another advantage of the present invention is that a method for treating a body part is provided that locates and stabilizes the body part in the same position during an radiographic imaging process and a surgical process.

The above and other advantages of the present invention are carried out in one form by an apparatus for locating a body part of a subject. The apparatus includes a support frame and a rigid template that is contoured to accommodate the body part and mounted to the support frame.

The above and other advantages of the present invention can also be carried out in another form by a method for treating a body part of a subject. The method involves the steps of placing the subject into the position that the subject will assume during a subsequent medical procedure, forming a rigid template to accommodate the body part, stabilizing the body part with the rigid template, and performing a medical procedure upon the body part.

BRIEF DESCRIPTION OF THE DRAWINGS

A more complete understanding of the present invention may be derived by referring to the detailed description and claims when considered in connection with the Figures, wherein like reference numbers refer to similar items throughout the Figures, and:

DETAILED DESCRIPTION OF THE PREFERRED EMBODIMENTS

Figure 1:
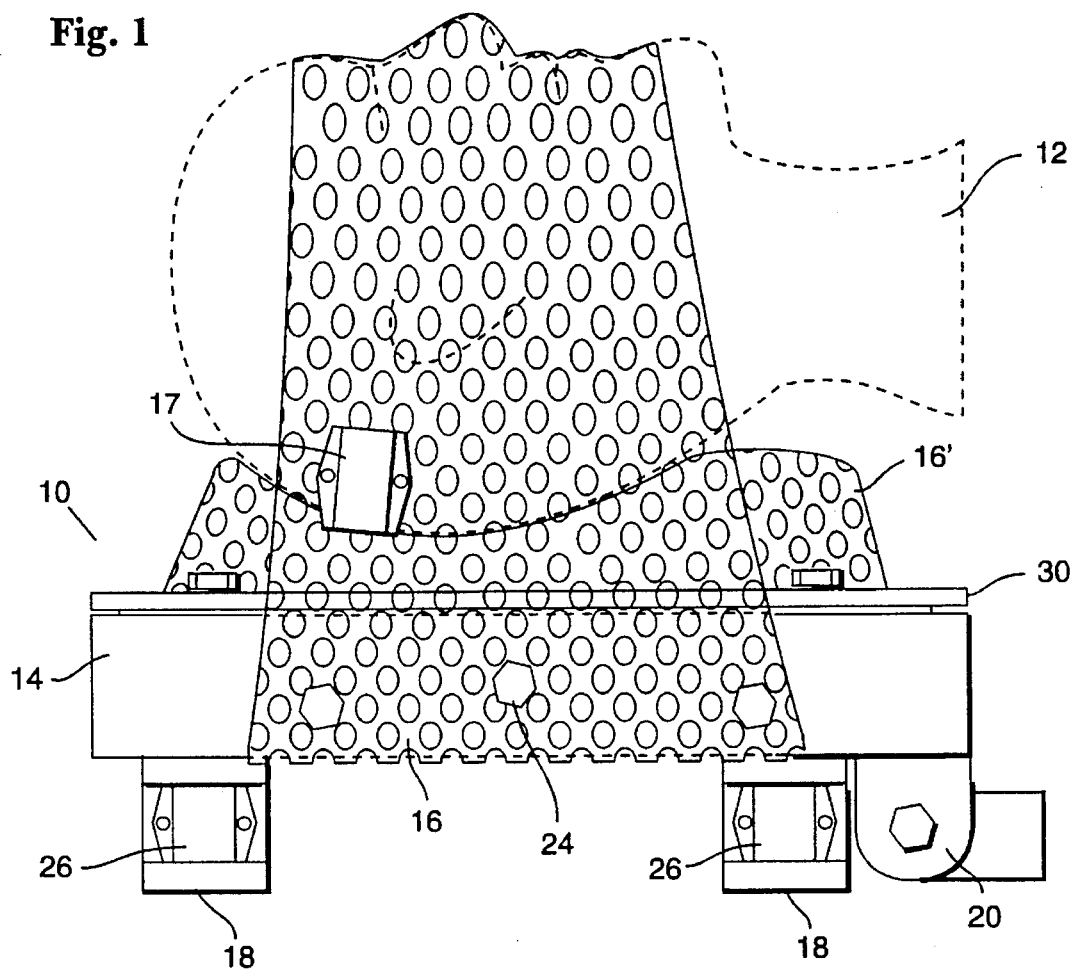
FIG. 1 shows a side view of an apparatus for locating a body part with a patient's head oriented in a supine position.
Figure 2:
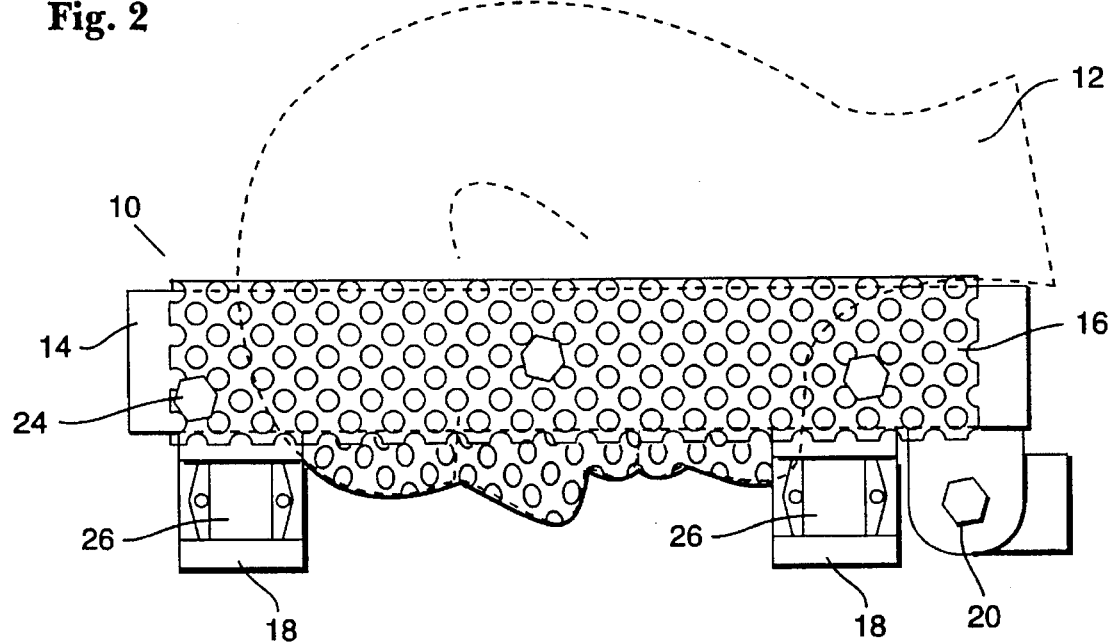
FIG. 2 shows a side view of an apparatus for locating a body part with a patient's head oriented in a prone position.

Referring to FIGS. 1–5, an apparatus 10 for stabilizing a body part is illustrated. In FIGS. 1–5, apparatus 10 is configured to locate the head of a subject. However, the present invention is not limited to the positioning or stabilization of the head, and apparatus 10 may be configured to stabilize other body parts as well. FIG. 1 depicts apparatus 10 securing a patient's head 12 (shown in phantom) in a supine position, while FIG. 2 depicts apparatus 10 supporting a patient's head 12 (shown in phantom) in a prone position. Although not shown, patient's head 12 may be oriented in other positions as needed. Apparatus 10 includes a support frame 14, a rigid template 16, a plurality of fiducial marker housings 18, and a mounting assembly 20.

Figure 3:
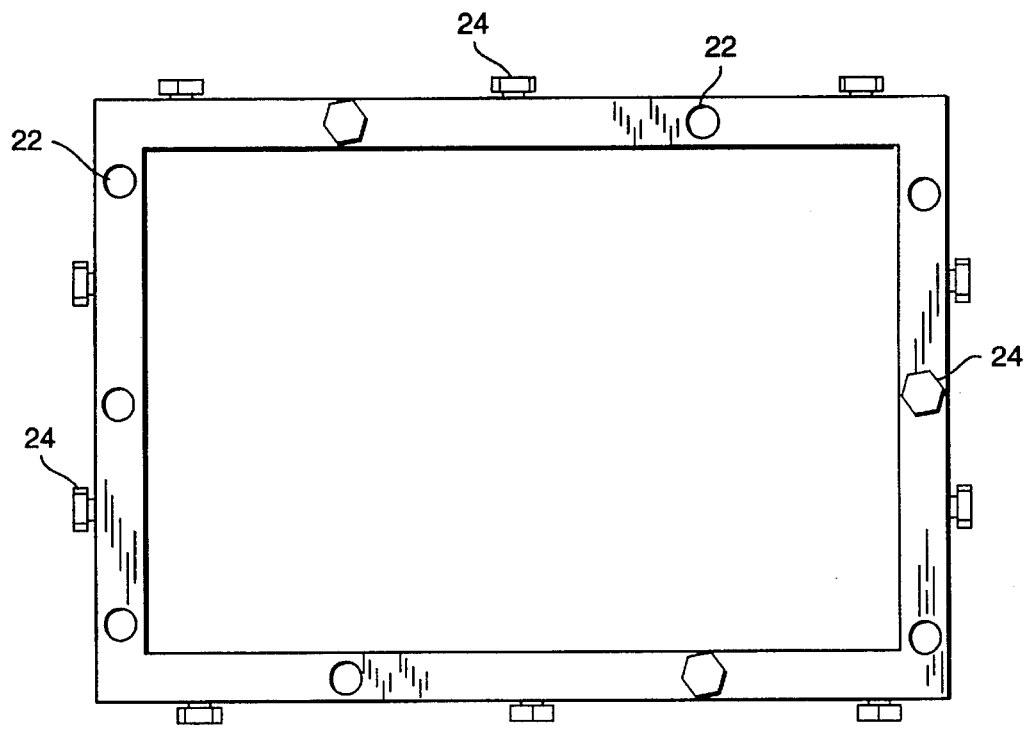
FIG. 3 shows a top view of a support frame according to the present invention.

With reference now to FIG. 3, support frame 14 is illustrated by itself. In this embodiment, support frame 14 is substantially rectangular in shape, and sized to create a stable foundation to support the head of a subject. Preferably, support frame 14 is formed from a plastic or nylon material, which is desirable during radiographic imaging so that unnecessary images or artifacts do not appear along with the image of the body part. For example, a steel frame distorts some CT and MRI images.

Support frame 14 includes a plurality of holes 22 for removably mounting rigid template 16 (described in detail below) to support frame 14. Preferably, holes 22 are located at multiple points around support frame 14, such as the outer perimeter, the inner perimeter, the top, and the bottom. The various locations of holes 22 facilitate the attachment of rigid templates having different shapes and sizes. Preferably, holes 22 are threaded to receive nylon or plastic bolts 24.

According to one aspect of the present invention, fiducial marker housings 18 are located on support frame 14. Passive fiducial markers provide reference points that appear on the images produced by an radiographic imaging process. In addition, active or passive fiducial markers may be placed in fiducial marker housings 18 to provide reference points that are used with frameless stereotactic localization techniques. Thus, fiducial marker housings 18 are sized to receive a diverse assortment of fiducial markers 26 that are well known in the medical field. The location and orientation of fiducial marker housings 18 may vary according to the specific imaging requirements. As such, although fiducial marker housings 18 are shown located on the bottom of support frame 14, the present invention is not limited to the depicted configuration. Therefore, fiducial marker housings 18 may be located on the top, outer perimeter, or inner perimeter of support frame 14 as needed.

Figure 4:
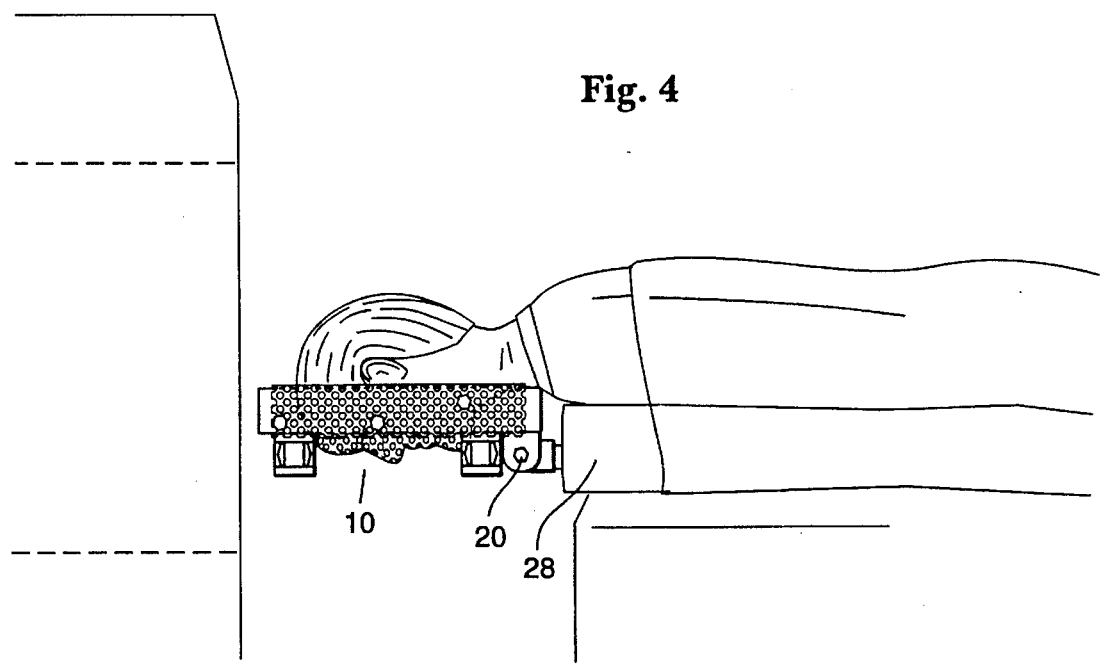
FIG. 4 shows the operational environment for an apparatus for locating a body part with a patient prepared to undergo an radiographic imaging procedure.

Mounting assembly 20 is also attached to support frame 14. Mounting assembly 20 is configured so that apparatus 10 can be attached to an operating table, radiographic imaging table, or other support structures. For example, FIG. 4 depicts apparatus 10 attached to a table 28. Preferably, mounting assembly 20 is pivotally attached to table 28 so that the angle between apparatus 10 and table 28 can be adjusted. According to one aspect of the preferred embodiment, mounting assembly 20 is configured to allow apparatus 10 to be alternatively mounted on a radiographic imaging table or an operating table. Thus, apparatus 10 can be used to stabilize or locate a patient's head in the same position during radiographic imaging and surgical procedures.

Rigid template 16 is removably mounted to support frame 14. Rigid template 16 is contoured to accommodate the head of the patient, whether the patient is in the prone, supine, or other position. According to the present invention, rigid template 16 is formed as a direct molding of the patient's head prior to a medical procedure such as radiographic imaging or surgery. Desirably, a surgeon or other medical practitioner dictates the patient position to best accomplish the medical procedure.

Preferably, rigid template 16 is formed from a thermally-activated moldable sheet of plastic that is softened, conformed to the patient's head, and cooled. Of course, the softening temperature must be low enough so that the patient can tolerate the direct molding process. A moldable plastic suitable for this purpose is commercially available under the name of Aquaplast. Of course, other materials such as fiberglass, plaster, foam, and the like may also be suitable for use in forming rigid template 16. After proper molding and cooling, rigid template 16 provides a personal fit for the support and stabilization of the patient's head by apparatus 10. In other words, rigid template 16 provides a rigid structure with a snug curve fit that follows the patient's unique features.

Rigid template 16 may additionally include a plurality of fiducial markers 17 affixed to it. In addition, rigid template 16 is preferably perforated (as shown) to accommodate patient comfort and to reduce erythema, and facilitate molding flexibility.

Figure 5:
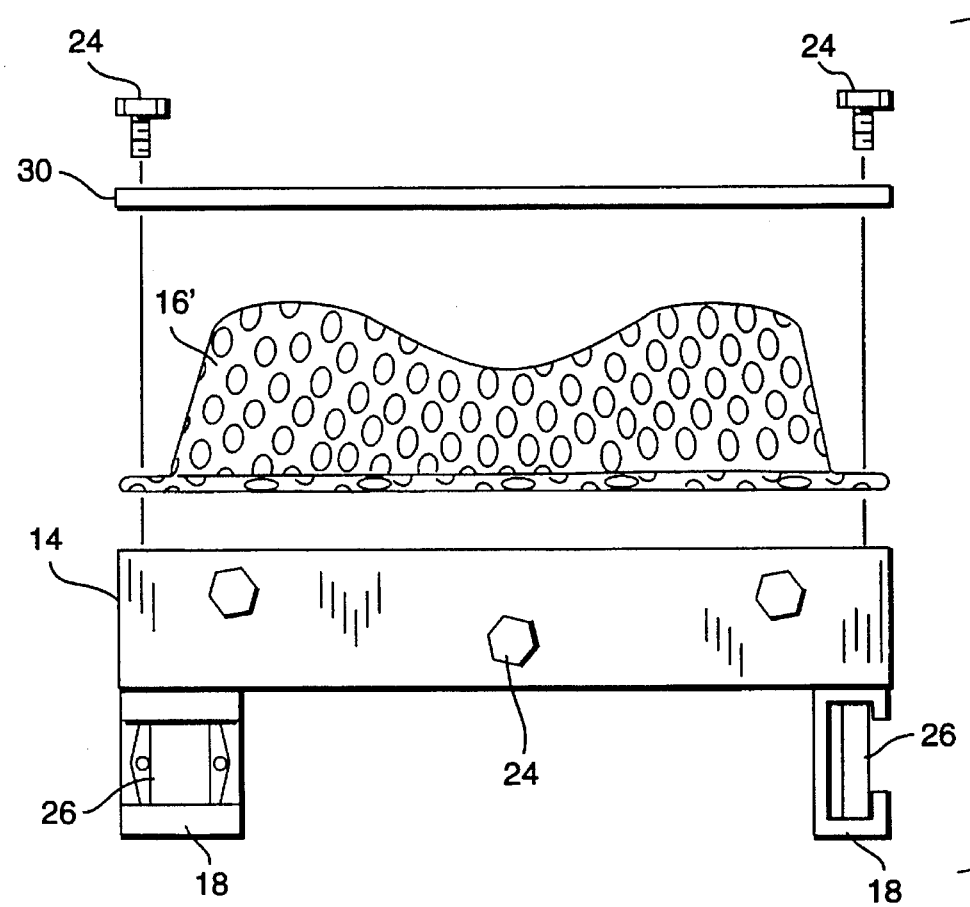
FIG. 5 shows an exploded frontal view of an apparatus according to the present invention.

As shown in FIGS. 2 and 4, rigid template 16 may be formed around the patient's face if subsequent medical procedures will be performed with the patient in the prone position. As shown in FIGS. 1 and 5, rigid template 16 may also include an element 16' molded to the back or side of the patient's head for use as a headrest. Element 16' may be attached to support frame 14 with a clamp 30 and bolts 24, as shown. Alternatively, element 16' may be attached directly to support frame 14 with bolts 24. Thus, when rigid template 16 is attached to table 28 via mounting assembly 20 (see FIG. 4), the head is effectively stabilized without utilizing fixating pins or other intrusive members.

An apparatus according to the present invention may be utilized in a method for treating a body part of a subject. Although the method will be described for medical procedures related to the head, the method may be applied to other body parts as well. Generally, the method involves the use of an apparatus as described above during an radiographic imaging process, followed by the use of the same apparatus during a surgical procedure.

Figure 6:
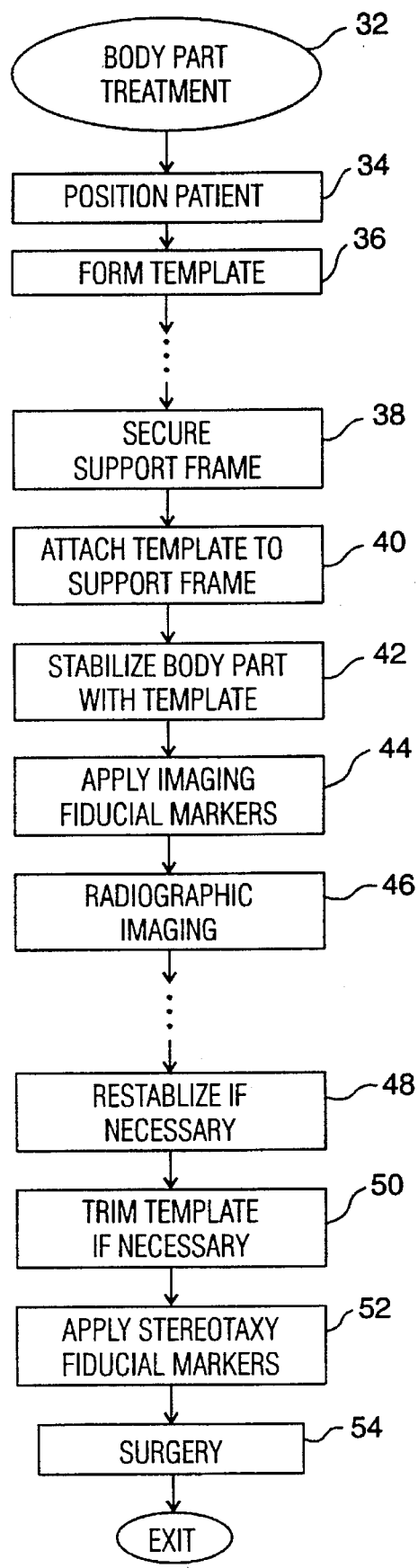
FIG. 6 is a procedure flow diagram for a method of treating a body part according to the present invention.

With reference to FIG. 6, a diagram illustrates the steps involved in a body part treatment procedure 32. A task 34 begins the procedure. In task 34, the patient may be placed into a position that the patient will assume during a later medical procedure. For example, if the patient will be in a prone position during surgery, then the patient may be placed in a prone position during task 34. Following task 34, a task 36 is performed. However, the patients' body can be repositioned during the surgical procedure within the conforming mold to facilitate the procedure.

In task 36, a rigid template is formed to accommodate the head or other body part of the patient. The above description of rigid template 16 may be referred to for more details. In the preferred embodiment, task 36 includes providing a thermally-activated moldable sheet of plastic (such as Aquaplast), heating the sheet of plastic until it becomes moldable, molding the sheet of plastic to follow the contours of the head and/or face, and cooling the sheet of plastic to produce the rigid template.

Preferably, the plastic sheet is heated by submerging it into a hot water bath. The temperature of the water is high enough to soften the plastic, and the precise temperature will depend upon the specific plastic used. For example, when Aquaplast is utilized to form the template, the water bath should be between 140° F. and 180° F. Due to the high temperatures involved, the molding process may have to be delayed until the temperature of the plastic is tolerable to the patient.

Due to the importance of having a repeatable reference position and the precision required during many surgical procedures involving the head, care must be taken during the molding process. For example, facial protrusions, contours, and bony areas such as the nose, cheeks, forehead, and chin should be accurately shaped. After molding the template, it remains on the patient until it has adequately cooled. When sufficiently cooled, the plastic becomes rigid and the template may be removed from the patient. If desired, body part treatment procedure 32 may be delayed after task 36 (indicated by the ellipses following task 36) if the actual stabilization or immobilization of the patient's head is not immediately required.

When it becomes time to actually stabilize the patient's head, a task 38 is performed. In task 38, a support frame is secured to a structure such as a bed or a table. A support frame according to the present invention is shown in FIGS. 1–3, and the previous description should be referred to for more details. After task 38 a task 40 is performed. In task 40, the cooled rigid template is attached to the support frame. As described above, the rigid template may include one element to support the back or side of the head and a second element to secure the head to the support frame. A task 42 follows task 40. In task 42, the patient's head is stabilized with the rigid template.

Depending upon the position of the patient, task 40 and task 42 may be performed in the opposite order. For example, if the patient is in a prone position, then the template is first attached to the support frame before the patient's head is placed in the apparatus (see FIGS. 2 and 4). However, if the patient is in a supine position, then a portion of the template may be attached after the patient's head is placed in the apparatus (see FIG. 1). In either case, following task 42 the head is effectively stabilized for subsequent treatment.

After stabilizing the patient's head, a radiographic imaging procedure (such as a CT, PET, or MRI scan) may be performed. With modern stereotactic and computer aided surgical techniques, such imaging of the head is desirable. As discussed above, it is often advantageous to have the patient's head in the same position during imaging and surgery. In a task 44, imaging fiducial markers are attached to the support frame, the rigid template, or both. As described above, an apparatus according to the present invention includes fiducial marker housings located on the support frame, and the rigid template may include additional fiducial markers affixed to it. Different types and sizes of imaging fiducial markers may be utilized depending upon the specific radiographic imaging process or the images desired by the treating physician.

After task 44, a task 46 involves performing the actual radiographic imaging process. For example, task 46 may involve a CT, MRI, or PET scan procedure. These processes are well known to those skilled in the art, and will not be described herein. The resulting images may be used for examination purposes or for subsequent stereotactic localization and surgical techniques.

Following task 46, body part treatment procedure 32 may be delayed before proceeding to surgery (indicated by the ellipses following task 46). If so, then the patient may be removed from the positioning device for a period of time. If the patient was removed from the positioning device, then a task 48 is later performed. Task 48 restabilizes the patient by repeating tasks 38, 40, and 42 (as necessary) prior to surgery. In addition, a task 50 may be performed, if necessary. Task 50 involves the trimming of excess material from the rigid template to provide access to the area to be operated on. To maintain the integrity of the rigid template, only the necessary amount of material should be removed for exposure. However, in some applications a sufficient portion of the rigid template may be removed to provide ample room for the use of retractors. The template may be sterilized if necessary before surgery to allow its inclusion in the sterile surgical field. Preferably, the fiducial marker locations are not disturbed during task 50. Following task 50, a task 52 may be performed if necessary.

In task 52, passive or active stereotaxy fiducial markers are inserted into the fiducial marker housings for use by a stereotactic localization system. Preferably, the stereotaxy fiducial markers are substituted for the imaging fiducial markers so that common points may be referenced during surgery. Stereotaxy fiducial markers provide feedback display information to the surgeon relative to a reference point such as a surgical instrument. Of course, if a stereotactic procedure will not be utilized, then task 52 is bypassed. Task 52 leads to a task 54.

Task 54 involves the actual surgical procedure with the patient's head stabilized in the same position that was used for the imaging process. The surgeon may refer to images obtained from the previous radiographic imaging process while utilizing the reference points corresponding to the fiducial markers located on the support frame or template in accordance with a frameless stereotactic localization system. In addition, the surgeon may be guided by endoscopic images and/or a real-time frameless stereotactic system display which produces images in response to the stereotaxy fiducial markers.

Following task 54, body part treatment procedure 32 ends. Of course, the patient will be removed from the stabilization apparatus and treated according to normal post-operation procedures.

In summary, the present invention provides an improved apparatus and method for immobilizing a body part that can be effectively utilized to stabilize the head of an adult, infant, or child. In addition, the present invention provides an apparatus and method for locating a body part that can be utilized to repeatedly locate the body part in the same position. Furthermore, a method for treating a body part is provided that locates the body part in the same position during a radiographic imaging process and a subsequent frameless stereotaxy assisted surgical process.

The above description is of preferred embodiments of the present invention, and the invention is not limited to the specific embodiments described and illustrated. For example, although the embodiments have been directed towards stabilizing the head of a subject, the invention is not limited to that particular body part. As another example, although Aquaplast may be a preferred material for use in the present invention, other materials may be used by those skilled in the art. In addition, descriptors such as above, bottom, and top have been used in an ordinary and relative sense to remain consistent with the Figures, and they are not to be construed in a limiting manner. Furthermore, many variations and modifications will be evident to those skilled in this art, and such variations and modifications are intended to be included within the spirit and scope of the invention, as expressed in the following claims.

What is claimed is:

1. An apparatus for locating a body part of a subject, said apparatus comprising:

a support frame;

a rigid template mounted to said support frame, said rigid template being contoured to accommodate said body part; and means for interchangeably holding a plurality of radiographic imaging fiducial markers and a corresponding plurality of stereotaxy fiducial markers at substantially common reference points relative to said body part when said body part is positioned with said rigid template.

2. An apparatus according to claim 1, further comprising means for mounting said support frame onto a structure.

3. An apparatus according to claim 1, further comprising a plurality of fiducial markers removably attached to said rigid template.

4. An apparatus according to claim 1, wherein said rigid template is formed as a molding of said body part.

5. An apparatus according to claim 4, wherein said rigid template is formed from a thermally-activated moldable sheet of plastic.

6. A method for treating a body part of a subject, said method comprising the steps of:

forming a noninvasive rigid template to accommodate said body part;

positioning said body part with said rigid template;

locating a plurality of radiographic imaging fiducial markers proximate said rigid template;

performing a radiographic imaging procedure upon said body part such that said imaging fiducial markers indicate a corresponding number of reference points relative to said body part;

replacing a number of said imaging fiducial markers with a corresponding number of stereotaxy fiducial markers; and performing a stereotactic localization procedure with said body part positioned with said rigid template such that said stereotaxy fiducial markers indicate a number of said reference points.

7. A method according to claim 6, wherein said rigid template positions said body part to provide approximately common reference points during said radiographic imaging procedure and said stereotactic localization procedure.

8. A method according to claim 6, wherein said locating step comprises the step of attaching said imaging fiducial markers onto said rigid template.

9. A method according to claim 6, wherein said locating step comprises the step of attaching said imaging fiducial markers onto a support frame coupled to said rigid template.

10. A method according to claim 6, further comprising the step of performing a stereotactically-guided surgical procedure upon said body part, said surgical procedure occurring after said replacing step and with said body part positioned with said rigid template, and said stereotaxy fiducial markers providing guidance information utilized during said surgical procedure.

* * * * *